United States Patent [19]
Berger

[11] Patent Number: 5,560,368
[45] Date of Patent: Oct. 1, 1996

[54] METHODOLOGY FOR AUTOMATED QT VARIABILITY MEASUREMENT

[76] Inventor: Ronald D. Berger, 3101 Northbrook Rd., Baltimore, Md. 21208

[21] Appl. No.: 340,861

[22] Filed: Nov. 15, 1994

[51] Int. Cl.$^6$ .................................................. A61B 5/0452
[52] U.S. Cl. ............................. 128/703; 128/702; 128/705
[58] Field of Search ........................................ 128/702, 703

[56] References Cited

U.S. PATENT DOCUMENTS

| | | | |
|---|---|---|---|
| 4,422,459 | 12/1983 | Simson | 128/702 |
| 4,802,491 | 2/1989 | Cohen et al. | 128/702 |
| 5,048,521 | 9/1991 | Pless et al. | 607/4 |
| 5,137,025 | 8/1992 | Turner, II | 128/695 |
| 5,209,228 | 5/1993 | Cano et al. | 607/27 |
| 5,217,021 | 6/1993 | Steinhaus et al. | 128/702 |
| 5,419,338 | 5/1995 | Sarma et al. | 128/703 |
| 5,437,285 | 8/1995 | Verrier et al. | 128/702 |
| 5,456,261 | 10/1995 | Luczyk | 128/702 |

OTHER PUBLICATIONS

Verrier and Nearing, *Electrophysiologic Basis for T Wave Alternans as an Index of Vulnerability to Ventricular Fibrillation*, Journal of Cardiovascular Electrophysiology, vol. 5, No. 5, May 1994, pp. 445–461.

Barr, et al., *QT Dispersion and Sudden Unexpected Death in Chronic Heart Failure*, The Lancet, vol. 343, Feb. 5, 1994, pp. 327–329.

Rosenbaum, et al., *Electrical Alternans and Vulnerability to Ventricular Arrhythmias*.

Merri, et al., *Dynamic Analysis of Ventricular Repolarization Duration from 24–Hour Holter Recordings*, IEEE Transaction on Biomedical Enginerring, vol. 40, No. 12, Dec. 1993, pp. 1219–1225.

Sarma, et al., *Circadian and Power Spectral Changes of RR and QT Intervals During Treatment of Patients with Angina Pectoris with Nadolol Providing Evidence for Differential Autonomic Modulation of Heart Rate and Ventricular Repolarization*, The American Journal of Cardiology, vol. 74, Jul. 15, 1994, pp. 131–136.

Algra and Zeelenberg, *An Algorithm for Computer Measurement of QT Intervals in the 24 Hour ECG*, IEEE, 1987, pp. 117–119.

Pisani, et al., *Performance Evaluation of Algorithms for QT Interval Measurements in Ambulatory ECG Recording*, IEEE, 1985, pp. 459–462.

Laguna, et al., *New Algorithm for QT Interval Analysis in 24–Hour Holter ECG: Performance and Applications*, IFMBE, 1990.

*Primary Examiner*—William E. Kamm
*Assistant Examiner*—Carl H. Layno
*Attorney, Agent, or Firm*—Henderson & Sturm

[57] ABSTRACT

A method for analyzing electrocardiograph signals to determine risk of malignant arrhythmias, that involves: sensing fluctuations in voltage resulting from electrical activity of a heart over a time period of about 256 seconds as signals having an analog value; converting such signals having an analog value to digital values corresponding substantially to the analog value of the signals; recording the digital values in a record; analyzing the digital values of the record by: identifying a time of each R wave of a heartbeat; defining a template QT interval for a heartbeat by selecting a beginning of a QRS complex and an end of a T wave for the heartbeat; determining an alteration value selected from the group consisting of an elongation of a heartbeat in time and a compression of a heartbeat in time as an error function for the heartbeat; performing a binary search to determine a minimal value for the error function; and assessing changes in QT interval for each heartbeat using the entire T wave.

16 Claims, 5 Drawing Sheets

QT Variability Algorithm

METHODOLOGY FOR AUTOMATED QT VARIABILITY MEASUREMENT

TECHNICAL FIELD

The present invention is directed to electrocardiogram analysis techniques to determine risk for subsequent malignant arrhythmias based on measurement of beat-to-beat variability in repolarization duration. Related to this, the present invention is directed methods for automated QT variability measurements, and specifically to such measurements which involve a QT interval assessment based on substantially the entire QT interval.

BACKGROUND

Sudden death due to lethal ventricular arrhythmias is a leading cause of mortality in the United States of America and throughout western civilization. It occurs unpredictably and usually without warning symptoms. Prior to the present invention, it is not believed that current methodology existed which provides adequately reliable risk stratification to identify which individuals are most in need of the limited and expensive resources required to prevent sudden cardiac death.

Sudden cardiac death (SCD) remains a public health problem in the United States with an incidence of 300,000 to 400,000 per year. SCD accounts for approximately half of all cardiac deaths. Ventricular fibrillation (VF) is the first documented rhythm in the vast majority of patients resuscitated from SCD, although holter monitoring has shown that VF is usually initiated by a period of rapid or polymorphic ventricular tachycardia (VT).

Cardiac mortality is particularly high among patients with congestive heart failure (CHF) and cardiac chamber enlargement, termed dilated cardiomyopathy (DCM). This syndrome has many etiologies including coronary artery disease, valvular heart disease, and myocarditis, although frequently no specific cause is identified. &renal death rates in these patients are as high as 25–40%.

Recent work has been directed toward identifying electrical abnormalities associated with DCM. Human studies and animal models of DCM reveal significant prolongation of action potential duration (APD) in cells isolated from failing hearts, regardless of etiology, compared to those taken from normal hearts. The plateau and terminal repolarization phases of the action potential are known to be quite labile. Membrane resistance is high at this time, and small changes in current can shift the balance toward either further repolarization or extended depolarization. It is generally believed that the longer the APD, the more labile is the repolarization process. Maintained or secondary depolarizations, also referred to as early after-depolarizations (EADs), can initiate triggered arrhythmias, including torsade de pointes, a form of polymorphic W and lead to VF. The presence of hypokalemia, hypocalcemia, hypomagnesemia, acidosis, or antiarrhythmic drugs, all common in patients with CHF, can affect either outward (repolarizing) or inward (depolarizing) currents and promote EADs.

The failing myocardium displays not only prolonged APD, but increased spatial heterogeneity of APD as well as resulting in an increase in dispersion of refractoriness. In such a substrate, a wave of depolarization is likely to encounter islands of refractory tissue, potentially leading to polymorphic ventricular arrhythmias through a mechanism of functional reentry. The cellular electrophysiologic basis for heterogeneity of APD may be multi-factorial. Regional variations in $K^+$ current densities, particularly $I_W$ have been reported in animal models. Heterogeneity of sympathetic innervation has also been described in patients with DCM and has been correlated with dispersion of refractoriness.

A number of tests, both invasive and noninvasive, have been employed as risk stratifiers of cardiac mortality in patients with CHF. Left ventricular election fraction (LVEF) has been shown to predict mortality in patients with schemic and nonischemic DCM. However, while total mortality increases with declining LV function, the fraction of deaths that are sudden has been observed to be highest in patients with the least severe disease. Furthermore, as discussed above, the population of patients with moderate to severe LV dysfunction is huge, so risk stratification by LVEF alone is insufficient.

The value of ambulatory monitoring and detection of asymptomatic ventricular ectopic activity (VEA) has been controversial. The presence of VEA has been shown to correlate with increased risk of SCD in survivors of myocardial infarction, although the sensitivity of this test for SCD is only approximately 30% and the specificity is lower. Furthermore, in a study in which ambulatory monitoring was used to predict drug efficacy for suppression of life-threatening arrhythmias in MI survivors, patients taking the active drug had sudden death rates in excess of those in a placebo treated group, thus demonstrating the inability of ambulatory monitoring to predict drug prearrhythmia. In patients with idiopathic DCM, high grade VEA has a prevalence of roughly 50% and essentially no predictive value. Similarly, exercise testing is not believed to be particularly useful in predicting SCD, as malignant arrhythmias are rarely provoked by such tests, even in high risk patient populations.

Signal-averaged electrocardiography (SAECG), which detects low amplitude electrical activity on the tail of the QRS complex reflective of slowed conduction required for reentry, has also been studied as a noninvasive means of stratifying arrhythmic risk. This methodology is not believed to be particularly useful in the setting of a bundle branch block, a common finding among patients with DCM, as it is believed that subtle late potentials would be masked. The SAECG has been observed to be moderately predictive of inducibility to monomorphic VT among survivors of a previous inferior MI, although less so in the setting of prior anterior MI. A number of studies have also demonstrated that the SAECG is predictive of SCD and overall mortality following an MI and in patients with nonischemic cardiomyopathy.

Electrophysiologic (EP) testing is an invasive procedure that has been observed to be highly sensitive for monomorphic VT, particularly among MI survivors with the substrate for classical reentry. EP testing is also believed to be capable of predicting drug efficacy in patients with inducible sustained monomorphic VT. Polymorphic VT and VF are often induced during EP testing as well, but are not predictive of such arrhythmias occurring clinically. Furthermore, arrhythmias are generally not inducible in SCD survivors or in patients with nonischemic DCM. Thus, EP testing is believed to have a limited role in predicting SCD, as it is invasive and lacks both sensitivity and specificity for polymorphic arrhythmias.

It is believed that heart rate variability (HRV) can function as a marker of arrhythmic risk. Reduced HRV has been shown to correlate with increased risk of SCD in MI survivors. Patients with CHF, irrespective of etiology, have also been shown to have reduced HRV compared with controls. While HRV is believed to be influenced by both sympathetic and parasympathetic modulation, it is believed that a reduction in vagal tone constitutes the mechanism by which HRV is reduced and arrhythmias are promoted among MI survivors at increased risk. It is somewhat unexpected that HRV stratifies arrhythmic risk as well as it does, given that it reflects alterations in autonomic balance, not direct changes in ventricular electrical integrity.

It is well known that congenital or acquired prolongation of the electrocardiographic QT interval is associated with an increased risk of polymorphic VT, VF, and SCD as disclosed by Keren, A. et al. "Etiology, warning signals and therapy of torsades de pointes: A study of 10 patients," *Circulation*, vol. 64, pp. 1167–1174, 1981; and Akhtar, M., "Clinical spectrum of ventricular tachycardia", *Circulation*, vol. 82, pp. 156–173, 1990. QT prolongation produced in an animal model by administration of the potassium channel blocker cesium chloride also leads to the development of EADs, triggered activity, and torsade de pointes. While these and similar observations in humans underscore the importance of altered ventricular repolarization in the incidence of SCD, QT prolongation alone is believed to lack adequate specificity to serve as a useful predictor of malignant arrhythmias, and mechanistically may not be important without accompanying electrical abnormalities.

It is believed that increased dispersion of repolarization duration is at least as important as prolongation of repolarization in the genesis of polymorphic arrhythmias. Invasive monophasic action potential (MAP) recordings have demonstrated regional inhomogeneity of APD in patients with the long QT syndrome and ventricular arrhythmias and in association with decreased fibrillation thresholds in dogs. Indirect evidence of regional differences in repolarization duration has been obtained noninvasively by body surface potential mapping. It has been proposed that the difference between maximum and miningum QT interval measured on a 12-lead ECG, referred to herein as "QT dispersion", provides an assessment of arrhythmic risk in patients with the long QT syndrome. More recently, this measure has been evaluated in a variety of patient populations at risk for malignant arrhythmias. QT dispersion is believed to be an effective metric for risk stratification of polymorphic VT an SCD, as it is based on a mechanism directly reflective of an abnormal ventricular electrical milieu. However, several technical difficulties make the QT dispersion measurement problematic and difficult to automate. For example, it is hard to identify a reproducible morphologic point to mark the end of the T wave; it is also somewhat unclear whether or not to include U waves in the QT interval; and approaches for rate correction of the QT interval have been questioned. Furthermore, while the QT interval may be substantially unambiguous in a few ECG leads, computation of the QT dispersion requires accurate determination of the QT interval in all 12 standard surface leads. Manual measurement of QT dispersion is laborious, and values obtained by automated algorithms often differ significantly from those found manually.

There is emerging evidence that temporal variation of ventricular repolarization may be an important precursor to malignant arrhythmias. A number of investigators have observed alternans of T wave morphology prior to spontaneous arrhythmias in animal models, for example, as disclosed by Hellerstein, H. K. et al., "Electrical alternation in experimental coronary artery occlusion," *Am. J. Physiol.*, vol. 160, pp. 366–374, 1950; Russell, D. C. et al. "Transmembrane potential changes and ventricular fibrillation during repetitive myocardial ischaemia in the dog", *Br. Heart J.*, vol. 42, pp. 88–96, 1979; and Adam, D. R. et al., "Fluctuations in T-wave morphology and susceptibility to ventricular fibrillation," *J. Electrocardiology*, vol. 17, pp. 209–218, 1984. The mechanism of T wave alternans also has been investigated. It is believed that dispersed subpopulations of cells may be refractory on an alternate beat basis, giving risk to macroscopic electrical alternans, wavefront fractionation, and potential reentry, for example, as disclosed by Smith, I. M. et al., "Simple finite-element model accounts for wide range of cardiac dysrhythmias," *PNAS*, vol. 81, pp. 233–237, 1984. Alternatively, it is believed that T wave alternans may reflect alternation in action potential morphology among a subpopulation of cells, for example as disclosed by Verrier, R. L. et al., "Electrophysiologic basis for T wave alternans as an index of vulnerability to ventricular fibrillation," *J. Cardiovasc. Electrophysiol.*, vol. 5, pp. 445–461, 1994. An algorithm to quantify the magnitude of T wave alternans also has been developed, for example as disclosed by Smith, J. M. et al., "Electrical alternans and cardiac electrical instability," *Circulation*, vol. 77, pp. 110–121, 1988, which has been shown to correlate with VT inducibility during EP testing and with arrhythmia-free survival, for example as disclosed by Rosenbaum, D. S., et al., "Electrical alternans and vulnerability to ventricular arrhythmias," *NEJM*, vol. 330, pp. 235–241, 1994. These investigators found that a chronotropic challenge by invasive atrial pacing was required to elicit sufficient T wave alternans to permit risk stratification.

In view of the importance of repolarization lability in arrhythmogenesis and the utility of heart rate variability as a risk stratifier, it is believed that QT interval variability might be abnormal in the setting of an arrhythmogenic substrate and serve as a marker of risk. Diurnal variation in QT interval has been observed for some time, for example as disclosed by Browne, K. F., "Prolongation of the QT interval in man during sleep," *Am. J. Cardiol.*, vol. 52, pp. 55–59, 1983; and Bexton, R. S., et al., "Diurnal variation of the QT interval-influence of the autonomic nerve system," *Br. Heart J.*, vol. 55, pp. 253–258, 1986. However, it is believed that little work has been done relating to beat-to-beat fluctuations in QT interval because of the technical difficulties in automated QT interval measurement, and particularly in separating true subtle beat-to-beat changes in QT interval from measurement noise.

Several algorithms for automated QT interval determination have been suggested that attempt to identify the point where the T wave rejoins the baseline, for example as disclosed by Laguna, P. et al., "New algorithm for QT interval analysis in 24-hour holter ECG: performance and applications," *Med. & Biol. Eng. & Comp.*, vol. 28, pp. 67–73, 1990; Pisani, E. et al., "Performance evaluation of algorithm for QT interval measurements in ambulatory ECG recording, *Comp. in Cardiol.*, vol. 11, pp. 459–462, 1985; and Algra, A. et al., "An algorithm for computer measurement of QT intervals in the 24 hour ECG," *Comp. in Cardiol.*, vol. 13, pp. 117–119, 1987. However, it is believed these methods may be prone to erroneous results, even in the setting of low amplitude noise, since they depend critically on signal quality of the terminal T wave. Two reports are directed to the relationship between beat-to-beat heart rate and QT interval variability. Merri et al. studied 10 healthy volunteers and found that fluctuations in repolarization duration followed closely those in RR interval (Merri, M. et al., "Dynamic analysis of ventricular repolarization duration from 24-hour holier recordings," *IEEE Trans. Biomed. Eng.*, vol. 40, pp. 1219–1225, 1993). On the other hand, Sarma et al. found poor coherence between RR and QT interval fluctuations in 12 patients with stable coronary artery disease (Sarma, J. S. M. et al., "Circadian and power spectral changes of RR and QT intervals during treatment of patients with angina pectoris with nadolol providing evidence for differential autonomic modulation of heart rate and ventricular repolarization" *Am. J. Cardiol.*, vol. 74, pp. 131–136, 1994). In neither of these studies, however, were fluctuations in true QT interval measured. To avoid the above-mentioned technical difficulties, both groups analyzed the interval from the peak of the R wave to the peals of the T wave. However, this approach essentially ignores fluctuations in U waves and the terminal portion of the T wave, both of which are likely to reflect arrhythmogenic abnormalities in repolarization, such as EADs, should they occur, for example as disclosed by Jackman, W. M. et al., "Ventricular tachyarrhythmias related to early after depolarizations and triggered firing: Relationship to QT interval prolongation and potential therapeutic role for calcium channel blocking agents," *J. Cardiovasc. Electrophysiol.*, vol. 1, pp. 170–195, 1990.

Accordingly, algorithms previously developed to measure the entire QT interval are believed to be problematic for beat-to-beat QT variability analysis. These algorithms use some morphologic feature to define the point where the T wave ends and joins the baseline, e.g., a fall in the slope below some threshold level, as disclosed by Laguna, P. et al., "New algorithm for QT interval analysis in 24-hour holter ECG: performance and applications," *Med. & Biol. Eng. & Comp.*, vol. 28, pp. 67–73, 1990; Pisani, E. et al., "Performance evaluation of algorithm for QT interval measurements in ambulatory ECG recording, *Comp. in Cardiol.*, vol. 11, pp. 459–462, 1985; and Algra, A. et al., "An algorithm for computer measurement of QT intervals in the 24 hour ECG," *Comp. in Cardiol.*, vol. 13, pp. 117–119, 1987. At least one problem with such an approach related to the fact that the latter part of the T wave is generally quite flat so that any signal noise can significantly shift the point where the threshold condition is met and lead to erroneous QT interval values.

SUMMARY OF THE INVENTION

The present invention is directed to novel and unobvious QT interval measurement methods. The present invention is based at least in part on assessing QT intervals based on substantially the entire QT interval. The method for measurement of QT intervals of the present invention preferably involves defining a template QT interval by selecting the beginning of the QRS complex and the end of the T wave for one beat. Related to this, the method for measurement of QT intervals in accordance with the present invention involves the use of a novel and unobvious algorithm for QT interval measurement. The algorithm is then relied upon to determine the QT interval of all other beats by determining how much each beat must be stretched, i.e. elongated, or compressed in time so as to best match the template. In this way, changes in QT interval are assessed using the entire T wave instead of just on the peak of the T wave or the terminal portion of the T wave. The method of measurement of QT interval, utilizing algorithms, as described in more detail herein, in accordance with the present invention allows for detection of subtle beat-to-beat QT variability. The present invention is also directed to apparatus for QT interval measurement. The apparatus of the present invention includes means for sensing electrocardiographic signals and means for analyzing electrocardiographic signals in accordance with the present invention to determine risk for subsequent malignant arrhythmias, preferably wherein such apparatus includes an implantable device having sub-surface leads, selected from a group consisting of pacemakers and defibrillators, in addition to apparatus having surface leads.

DETAILED DESCRIPTION

The following is a detailed description relating to the present invention that is intended to be claimed.

Figure 9:
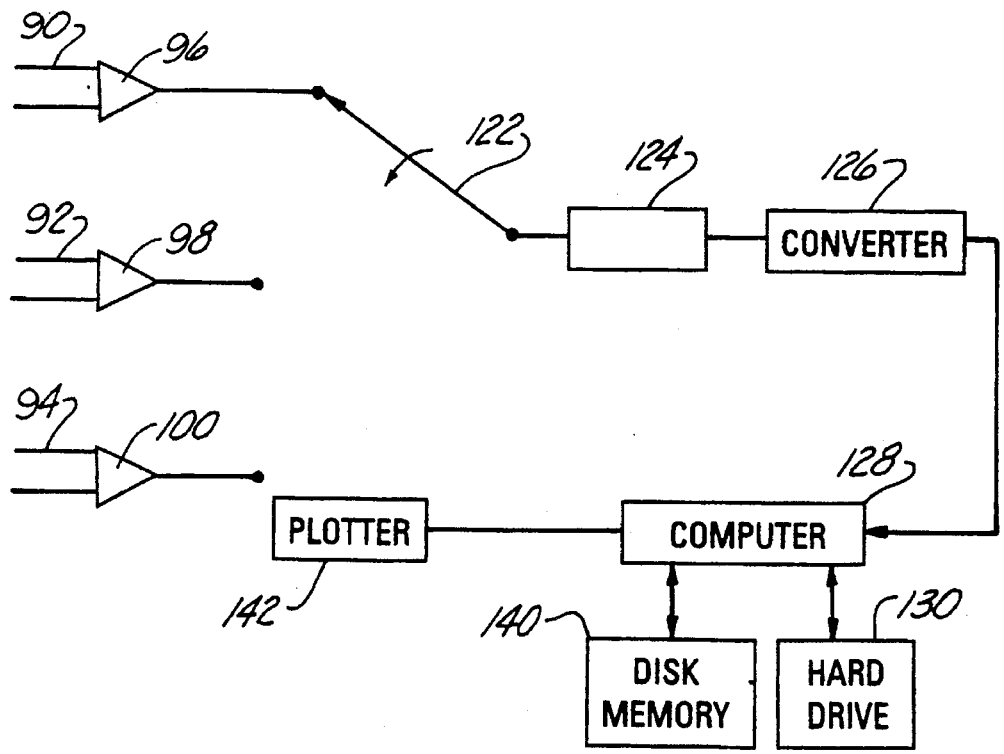
FIG. 9 is a simplified, functional, block diagram of an embodiment of the present invention.

The method for measuring QT intervals, that involves using novel and unobvious algorithms as described in more detail herein, in accordance with the present invention involves analyzing an ECG record. A simplified, functional, block diagram of an apparatus suitable for use in accordance with the invention is shown in FIG. 9. For purposes of the present invention only one lead 90 is necessary and required; however, a plurality of leads 90, 92 and 94 may be used. In any event, any or each of the leads 90, 92, and 94 may be a surface electrocardiographic or venticular lead, or a sub-surface lead if the apparatus comprises implantable devices, such as pacemakers and defibrillators. In the embodiment specifically described herein, the lead 90 may be any standard or surface lead no. 1 or no. 2 applied to the patient's body between the right and left arm, or between the right arm and left leg, respectively. Any or each of the leads (90, 92, 94) is fed respectively to amplifiers 96, 98, and 100. The output of each amplifier may be passed to a switch contact, through switch 122, and to a low pass filter 124. Filter 124 characteristically attenuates all signals below about 0.5 Hz and above about 200 Hz. The output from filter 124 is fed to an analog to digital converter 126 which samples the incoming voltage, most preferably every millisecond, and converts it to a 16-bit binary signal. The digitized wave form outputs from converter 126 are fed to computer 128, which then stores the data on hard or disk drive 130.

For purposes of the apparatus suitable for use in accordance with the present invention, the amplifier(s) and related hardware and software for digitization of the signals were commercially available as a Bio Pac™ package. The computer used was a 486 type computer commercially available as model Gateway 200.

The present invention, however, may be embodied in implantable apparatus, most preferably selected from the group consisting of pacemakers and defibrillators. This may be accomplished by adding microcircuitry logic incorporating algorithms suitable for purposes of the present invention to the microcircuitry logic of pacemakers and defibrillators wherein the previously mentioned lead(s) would be sub-surface, ventricular or intracardiac lead(s) that may be unipolar or bipolar. Accordingly, the present invention finds utility, not only to surface ECG applications, but also to intracardiac electrograms. Thus, the present invention may be used to assess cardiac electrical instability by implantable devices, such as pacemakers and defibrillators.

With the foregoing in mind, the present invention involves monitoring heart activity by means for monitoring heart activity selected from a group of heart monitoring apparatus having surface leads, including electrodes that may be attached to the exterior of a patient's body, such as electrocardiographic devices, and heart monitoring apparatus having sub-surface leads, including implantable apparatus selected from the group consisting of pacemakers and defibrillators. In any case, the leads detect the heart's electrical signals in accordance with the various phases of heart activity. The signals can be displayed in wave form on a monitor plotter 142 and/or recorded on a chart or computer hard drive 130 or disk 140. As described in more detail herein certain steps of the present invention are conducted with the aid of a digital computer 128 and the mathematical formulae or algorithms, described herein, are used to configure or program such computer. Related to this, dedicated specific purpose equipment or hard wired logic circuitry can be used in accordance with the present invention.

Accordingly, although mathematical calculations or algorithms, as described herein, may be involved in carrying out the claimed process, the present invention that is intended to be claimed includes methods of detection of a certain heart condition by a novel method of analyzing a portion of an electrocardiographically measured heart cycle. This is accomplished by procedures conducted by means of electronic equipment programmed to perform mathematical computations utilizing the algorithms as described herein.

These procedures include transforming the electrocardiographic signals from analog form, in which they are obtained, to corresponding digital signals which are related to a patient's heart function. The signals are then stored as a record, processed and analyzed in accordance with the present invention to determine whether a patient is at risk for malignant arrhythmias.

Related output is also a signal relating to the patient's heart activity.

Thus, in accordance with the present invention, the processes and/or methods of present invention intended to be claimed include physical process steps that transform one physical, electrical signal into another wherein the mathematical procedure and algorithms, as described herein, are applied to the physical process steps. In so doing, the present invention is at least in part directed to a method for analyzing electrograph signals in order to determine a specified heart activity, or electrocardiograph analysis process, wherein the mathematical formula or algorithms, as described herein, are used with process steps of the present invention as claimed.

The apparatus suitable for purpose of the present invention includes a combination of interrelated means for performing specified functions, as described herein. In this regard, the apparatus of the present invention intended to be claimed includes, in addition to means for sensing changes in electrical potential produced by contractions of a heart of a subject during a heartbeat, i.e., as an electrocardiograph signal, means for converting the electrocardiograph signals from the analog form in which they are generated into digital form. This means is an electronic device, i.e., a conventional analog-to-digital convertor 126. A computer 128 is a means of calculating in accordance with the present invention. The product is stored in the form of electrical signals. The hard drive 130 or disk memory unit 140 stores signals and other data. The apparatus also includes connecting leads to the computer's processing unit. The apparatus of the present invention thus defines a combination of interrelated means for performing specified function. The computer-performed operations transform a particular input signal to a different output signal, in accordance with the internal structure of the computer as configured by electronic instructions. Thus, the claimed invention converts one physical thing into another physical thing just as any other electrical circuitry would do.

The steps of the method for determining risk of malignant arrhythmias of the present invention that involve in analyzing an ECG record, which is most preferably a digitized ECG record, include:

(1) identifying the time of each R wave, preferably using a peak detection algorithm, wherein time locations are denoted $T_i$.

(2) Selecting the beginning and end of the QT interval for any one heartbeat, also referred to herein as beats denoted beat k, wherein a preferred template is denoted $$\phi(n)=x(n) \text{ from } n=n_0 \text{ to } n=n_1 \qquad (1)$$

where x(n) is the ECG signal and $n_0$ and $n_1$ are the beginning and end samples of the QT template, respectively. The most preferred template for purposes of the method for measuring QT intervals, that involves using the novel and unobvious algorithm, in accordance with the present invention has $N=n_1-n_0$ points, and the template QT interval duration is N $\Delta t$ where $\Delta t$ is the digitization interval (1 msec). For the purpose of matching all other beats to the template in accordance with the present invention, however, the algorithm ignores the actual QRS complex and uses only the ST segment and T wave. Thus, only the region of the template from $n=T_k+n_\nabla$ to $n=n_j$ is subsequently used, where $n_\nabla$ represents a preset delay, e.g. 50 mnsec. In embodiments where surface leads are used in a non-invasive method in accordance with the present invention, the beginning and end of a QT interval is preferably selected by an operator of the apparatus. In embodiments of the present invention wherein invasive procedure s have been used at least to implant sub-surface leads, and implanted apparatus, such as pacemakers and defibrillators comprising means for performing the functions described herein, the selection of the QT interval may be selected automatically without the involvement of an operation.

(3) For each beat, an error function $\epsilon_i(\alpha)$ is defined:

$$\epsilon_i(\alpha) = \sum_{j=n_\nabla}^{n_1-T_k} [\Phi(T_k+j) - \chi(T_i+\alpha j)]^2$$

where $\alpha$ is the time stretching factor. $\epsilon_i(\alpha)$ is thus the sum of squared differences between the template T wave and the stretched or compressed version of the T wave for beat i.

(4) A binary search is performed to find the value of a that minimizes $\epsilon_i(\alpha)$ for that beat. This, referred to as the best value of $\alpha$, is denoted $\hat{\alpha}_i$, and is generally between 0.95 and 1.05. The search proceeds until the search step size for $\alpha$ is less than 0.0001.

The QT interval for the $i^{th}$ beat is taken as $QT_i = \hat{\alpha}_i \, N \, \Delta t$ since, again, $N \, \Delta t$ is the duration of the template QT interval.

In accordance with the present invention, the determination of the end of the template T wave by the operator of the apparatus may be somewhat arbitrary within limits. Regardless, the end of the template T in accordance with the present invention should be matched morphologically from beat-to-beat. Thus, in accordance with the method for measuring QT intervals in accordance with the present invention if the operator chooses a point well before or well after the true end of the T wave, all QT interval values computed will be biased proportionately low or high, respectively; nevertheless, the beat-to-beat variability in computed QT intervals will be relatively unaffected. Furthermore, to the extent that repolarization lability resides in the latter portion of the T wave, or in the U wave if present, all deflections that may relate to repolarization may be included in the template. For purposes of the method for measuring QT intervals in accordance with the present invention, however, U waves do not have a disproportionate effect on the QT interval determination, since they are generally of low amplitude and will, therefore, influence the sum of squared differences as indicated in Equation 2 less than will the T wave.

Figure 1:
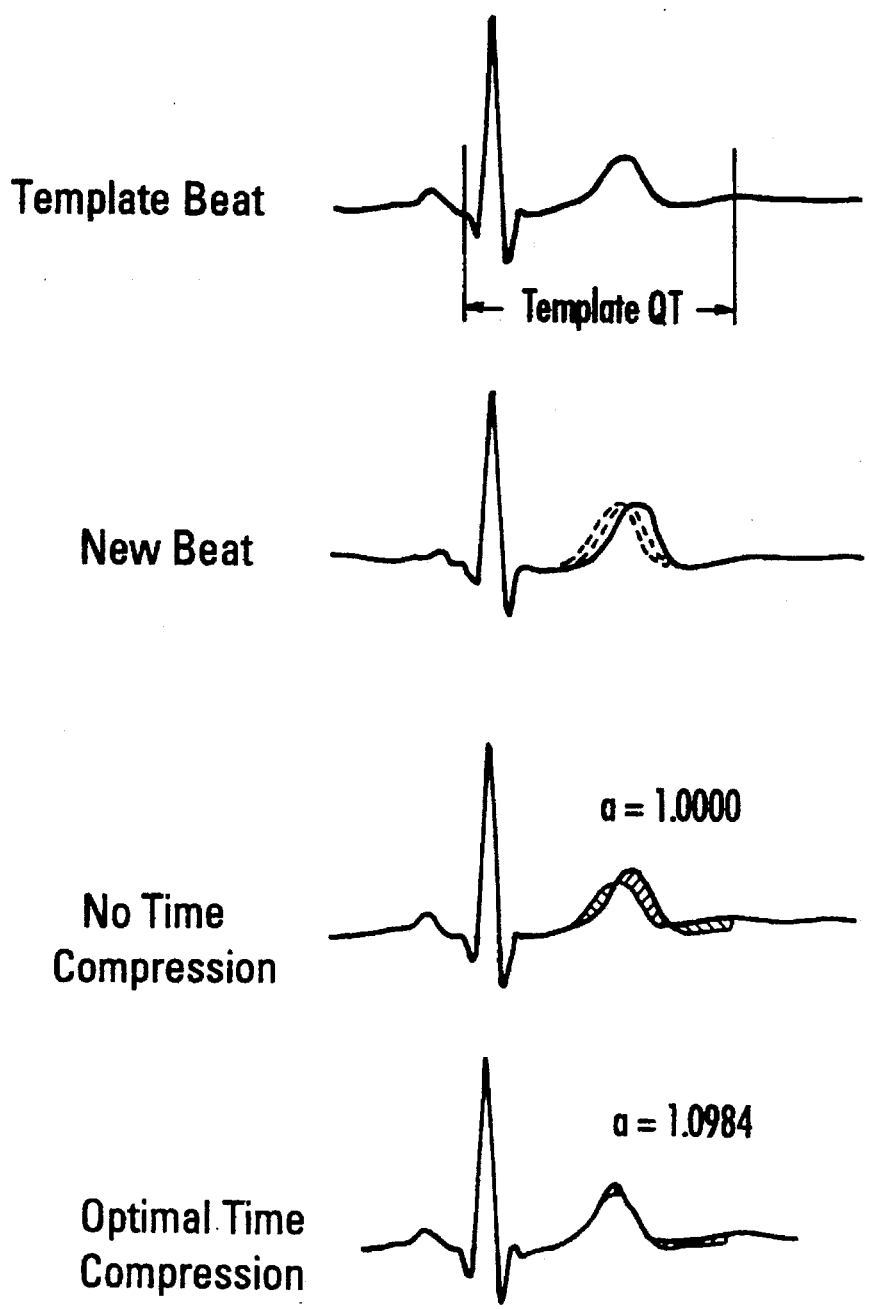
FIG. 1 is a graphical demonstration of an algorithm used in the method for measurement of QT intervals in accordance with the present invention.

The algorithm most preferred for use in the method for measuring QT intervals in accordance with the present invention is shown graphically in FIG. 1. The top panel shows the operator-selected template QT interval with the region used for the error function highlighted. A subsequent beat in the analysis is shown in the next panel, with several time-compressed versions of its T wave superimposed (dashed lines). The third panel shows the rather large area of difference between the template T wave and the uncompressed version of the index beat, while the bottom panel shows the close match between the template T wave and the optimally compressed version of this beat. The compression ratio $\hat{\alpha}$ that minimizes the difference between the template and the index beat in this case is 1.0984. The QT interval for this beat is thus taken as 1.0984 times the template QT interval.

A modification of this algorithm for use in the method for measuring QT intervals in accordance with the present invention can be used for determination of action potential duration (APD) from recordings of monophasic action potential (MAP). The activation times ($T_i$) are taken as the points of maximal phase 0 upstroke. In order to base APD on the entire action potential waveform the time delay following activation before the start of the template ($n_v$) is eliminated (set to 0). No other modification are required.

In accordance with the method for measuring QT intervals of the present invention, an evenly sampled instantaneous heart rate series is formed by resampling the inverse RR interval sequence at 4 Hz as described previously by Berger, R. D. et al., "An efficient algorithm for spectral analysis of heart rate variability," *IEEE Trans. Biomed. Eng.*, vol. BME-33, pp. 900–904, 1986, the disclosure of which is incorporated by reference thereto herein. A resampled QT interval series is similarly formed using an adaptation of substantially the same technique. In this way, instantaneous heart rate (HR) and QT interval can be plotted against real time instead of beat number. Artifacts in these resampled series caused by ectopic beats are removed, for example as disclosed by Saul, et al., "Assessment of autonomic regulation in chronic congestive heart failure by heart rate spectral analysis," *Am. J. Cardiol.*, vol. 61, pp. 1292–1299, 1988. The power spectrum of each of these signals is computed as the Fourier transform of the windowed autocorrelation function, using a Gaussian window as disclosed by Jenkins, G. M. et al., "Spectral Analysis and its Applications", *Holden-Day,* Oakland, Calif., 1968; Berger, R. D., "Analysis of the Cardiovascular Control System Using Broad-Band Stimulation" *Ph.D. Thesis,* M.I.T., 1987, the disclosure of which in its entirety is incorporated by reference thereto herein, and the cross-spectrum is taken as the Fourier transform of the windowed cross-correlation function between HR and QT interval. In accordance with the method for measuring QT intervals in accordance with the present invention, the total HR and QT variability power is determined by integrating the respective power spectra. A record length of 1,024 samples, representing 256 seconds (4 minutes 16 seconds), is most preferred for use in the spectral analysis. Although not wishing to be bound by any particular theory, it is believed that analysis based on shorter records would be subject to errors due to reduced frequency, resolution and increased estimator variance, and longer records would likely incur nonstationary in the data. Thus 256 seconds is most preferred.

The QT variability index (QTVI) is calculated as $$QTVI = \log_{10}(P_{QTV}/P_{HRV}) \quad (4)$$

where $P_{QTV}$ and $P_{HRV}$ represent total QT and HR variability power. The QTVI represents a simple measure of repolarization variability that is normalized by the degree of heart rate modulation. In accordance with the present invention, the QTVI can be modified so that the argument of the log function is unitless by normalizing the QT and HR variability powers as follows:

$$P'_{QTV} = P_{QTV}/<QT>^2 \quad (5a)$$

$$P'_{HRV} = P_{HRV}/<HR>^2 \quad (5b)$$

where $<QT>$ and $<HR>$ are the mean QT interval and heart rate, respectively. Then the modified QTVI is taken as $$QTVI' = \log_{10}(P'_{QTV}/P'_{HRV}) \quad (6)$$

The algorithm for tracing dynamic changes in QT interval used in the method for measuring QT intervals in accordance with the present invention presented above is based on measurement of a surface ECG lead. As discussed above, however, the algorithm method for measuring QT intervals in accordance with the present invention may also be applied to intracardiac electrograms without any modification, and may be used with implanted apparatus, such as pacemakers and defibrillators. Electrograms should be obtained with DC coupling or at least with the low frequency edge of the pass band below about 1 Hz so that deflections related to local myocardial repolarization will be preserved. Such electrograms are available via pacemaker or implantable defibrillator ventricular leads. Algorithms for pacemaker rate regulation based on the QT interval measured via the ventricular pacing lead are already in use. The QT variability algorithm may be incorporated into the logic circuitry of pacemakers and defibrillators to provide arrhythmic risk information to the patient's physician via telemetry. It is believed that this information is useful in predicting defibrillator firing events and in guiding antiarrhythmic drug management.

EXAMPLES

Figure 2:
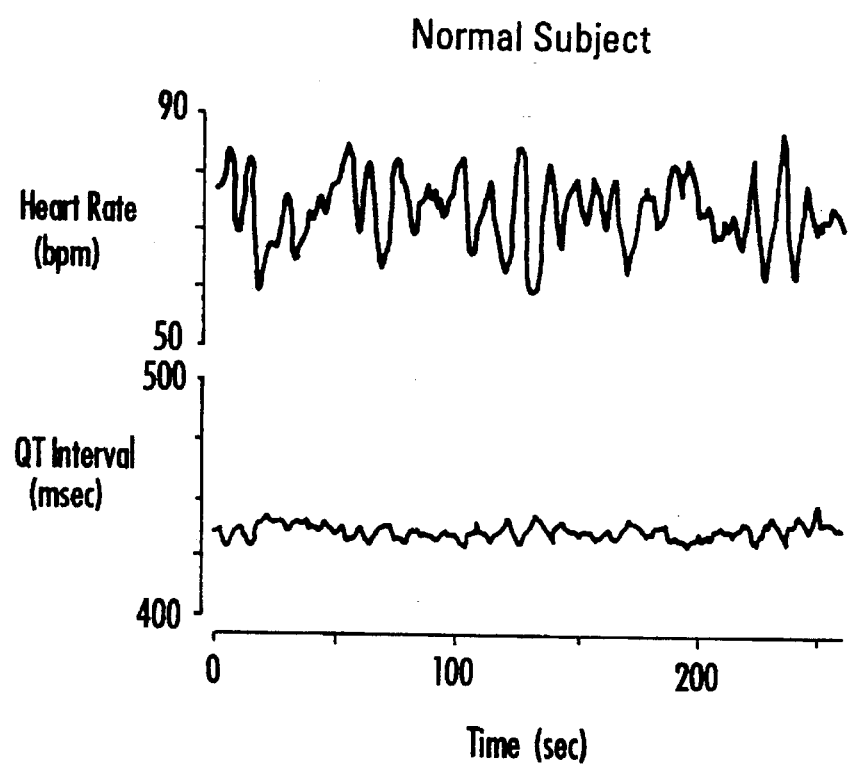
FIG. 2 shows simultaneous heart rate and QT interval fluctuations in a normal subject.

The following procedures in accordance with the method for measuring QT intervals in accordance with the present invention were conducted to study QT variability in a small cohort of patients with DCM and in a group of normal subjects. In this preliminary work, 256 second epochs of either lead I or II of the surface ECG were used in the analysis. Simultaneous heart rate and QT interval fluctuations in a normal subject are shown in FIG. 2. As indicated, there is substantial heart rate variability and beat-to-beat changes in heart rate are mirrored by those in QT interval.

Example 1

Figure 3:
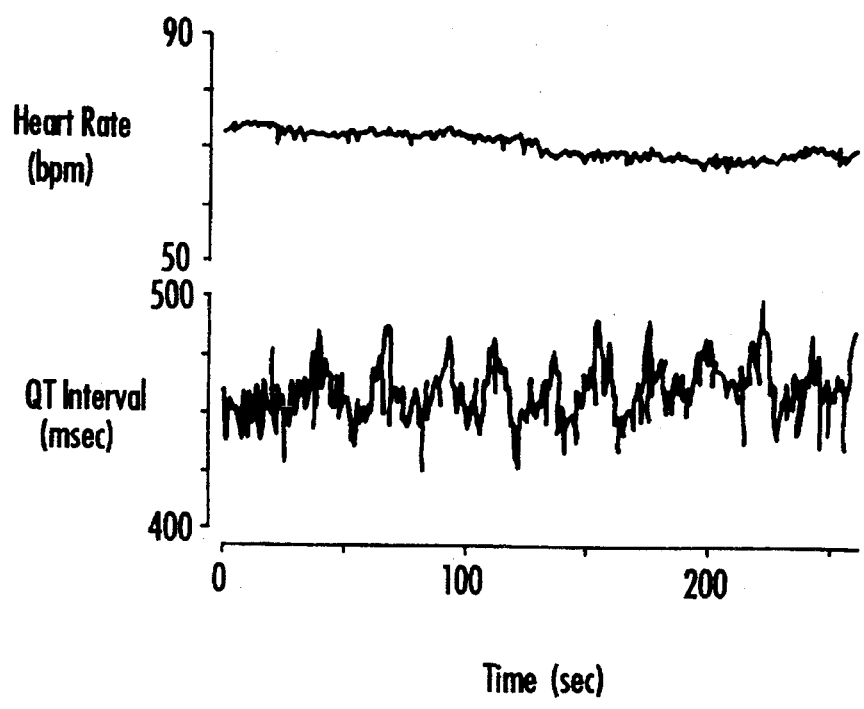
FIG. 3 shows an example of heart rate and QT variability in a patient with DCM presenting with frequent episodes of polymorphic VT.

In contrast, FIG. 3 shows an example of heart rate and QT variability in a patient with DCM presenting with frequent episodes of polymorphic VT who died of intractable VF two days after the recordings were made. In this case, heart rate fluctuations are small and QT interval oscillations are large. Also, and importantly, the QT interval fluctuations appear erratic and uncoupled from those in heart rate.

Figure 4:
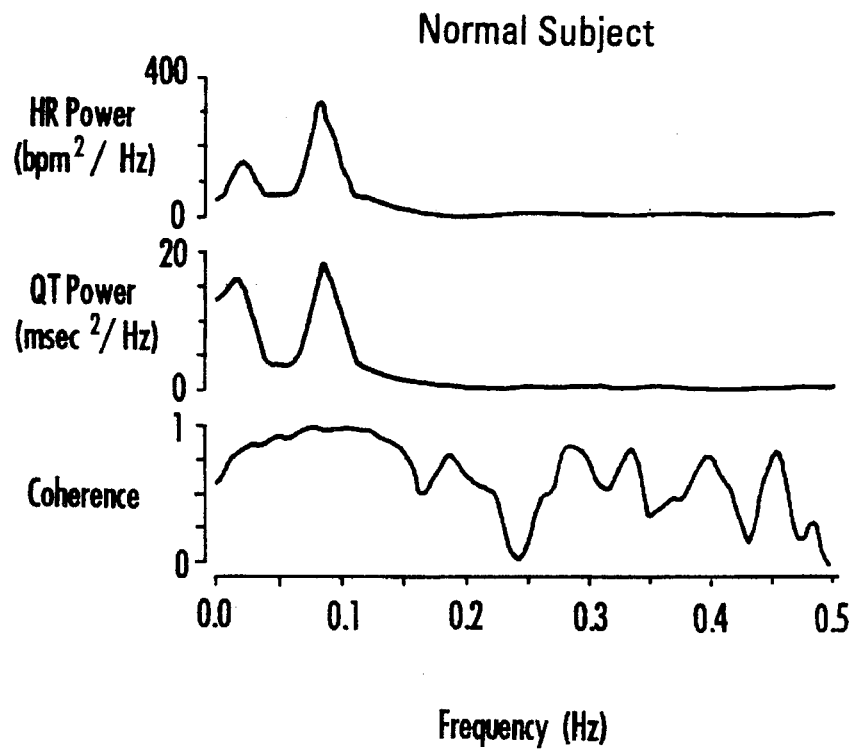
FIG. 4 shows power spectra of heart rate and QT interval oscillations from FIG. 2.
Figure 5:
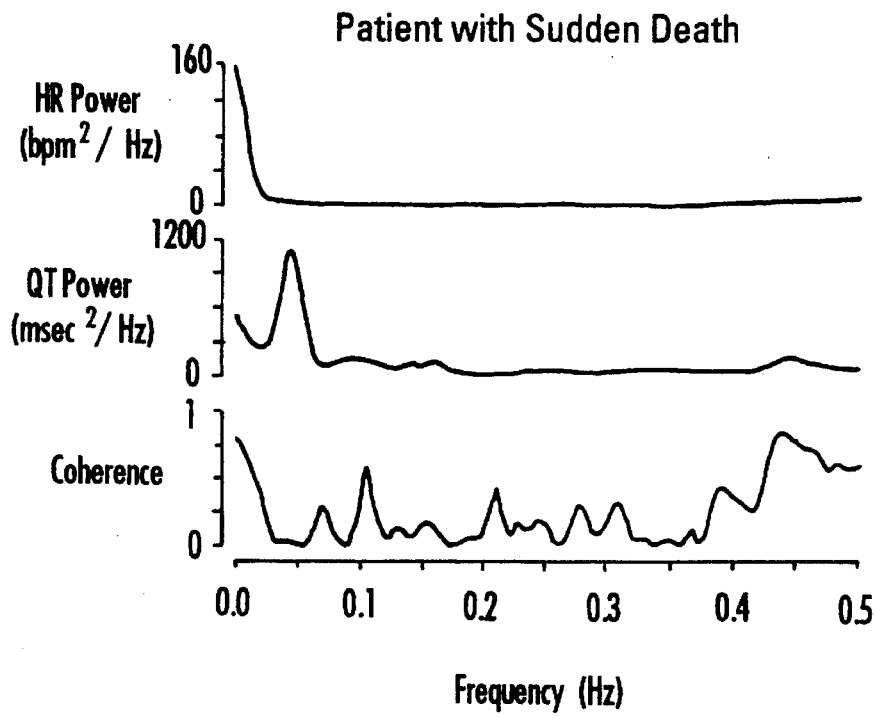
FIG. 5 shows power spectra of heart rate and QT interval oscillations from FIG. 3.

Power spectra of the heart rate and QT interval oscillations from FIGS. 2 and 3 are shown in FIGS. 4 and 5, respectively. The normal subject has significant HRV up to roughly 0.2 Hz and the shape of the HRV and QTV spectra are nearly identical. The patient with DCM, on the other hand, exhibits only very low frequency HRV, and the HRV and QTV spectra are dissimilar. Also shown in FIGS. 4 and 5 are the coherence spectra for the two cases. The coherence function $\gamma^2(f)$, ranges from zero to unity reflecting the degree to which oscillations with frequency $f$ in QT interval are linearly related to fluctuations at the same frequency in the heart rate $\gamma^2(f)$ is defined as:

$$\gamma^2(f) = \frac{|S_{rq}(f)|^2}{S_{rr}(f)S_{qq}(f)} \quad (7)$$

where $S_{rr}(f)$ is the power spectrum of the resampled heart rate series, $S_{qq}(f)$ is the prover spectrum of the resampled QT interval series, and $S_{rq}(f)$ is the cross spectrum between the two processes. For a normal subject, heart rate and QT intervals fluctuations are reasonably coherent over a broad range of frequencies, whereas for the patient with DCM heart rate and QT variability lack coherence at most frequencies. These discoveries are consistent with the two reports regarding repolarization variability, disclosed by Merri, M. et al., "Dynamic analysis of ventricular repolarization duration from 24-hour holter recordings," *IEEE Trans. Biomed. Eng.*, vol. 40, pp. 1219–1225, 1993; and Sarma, J. S. M. et al., "Circadian and power spectral changes of RR and QT intervals during treatment of patients with angina pectoris with nadolol providing evidence for differential autonomic modulation of heart rate and ventricular repolarization" *Am. J. Cardiol.*, vol. 74, pp. 131–136, 1994.

Example 2

Figure 6:
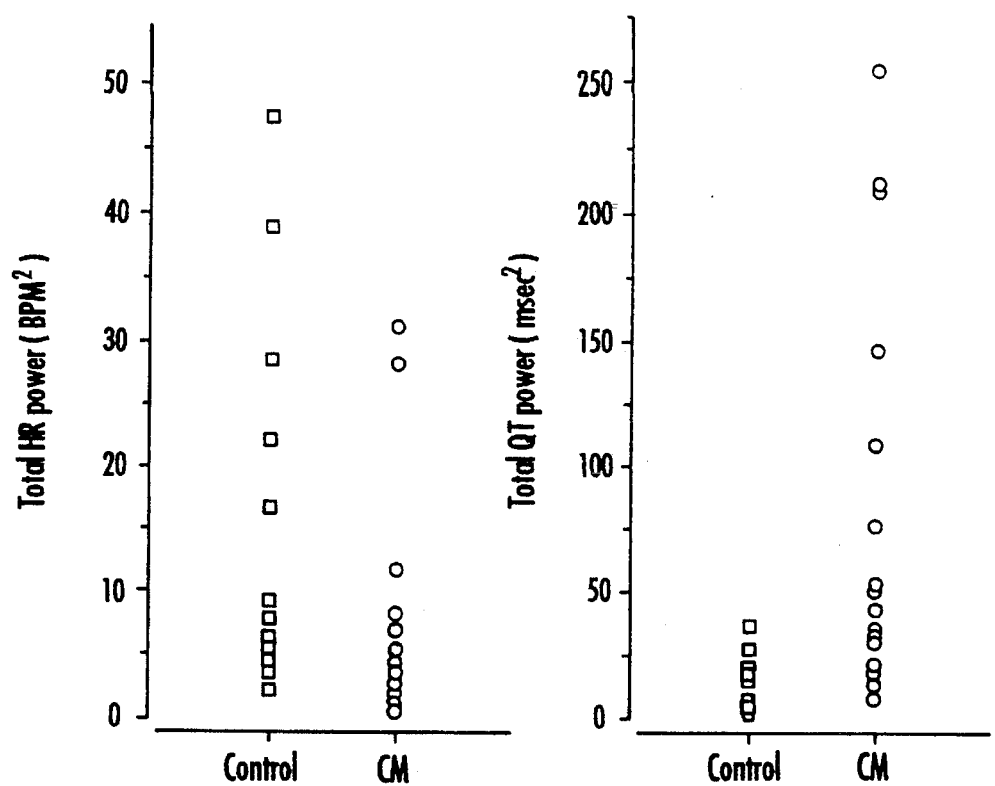
FIG. 6 shows the total power or variance in the heart rate and QT variability among a number of patients with DCM and normal controls.

FIG. 6 shows the total power (or variance) in the heart rate and QT variability among 24 patients with DCM and 12 normal controls. Significant differences were found, with DCM patients displaying reduced HRV and greater QTV than controls, although there is substantial overlap in the range of values found for both parameters.

Example 3

Figure 7:
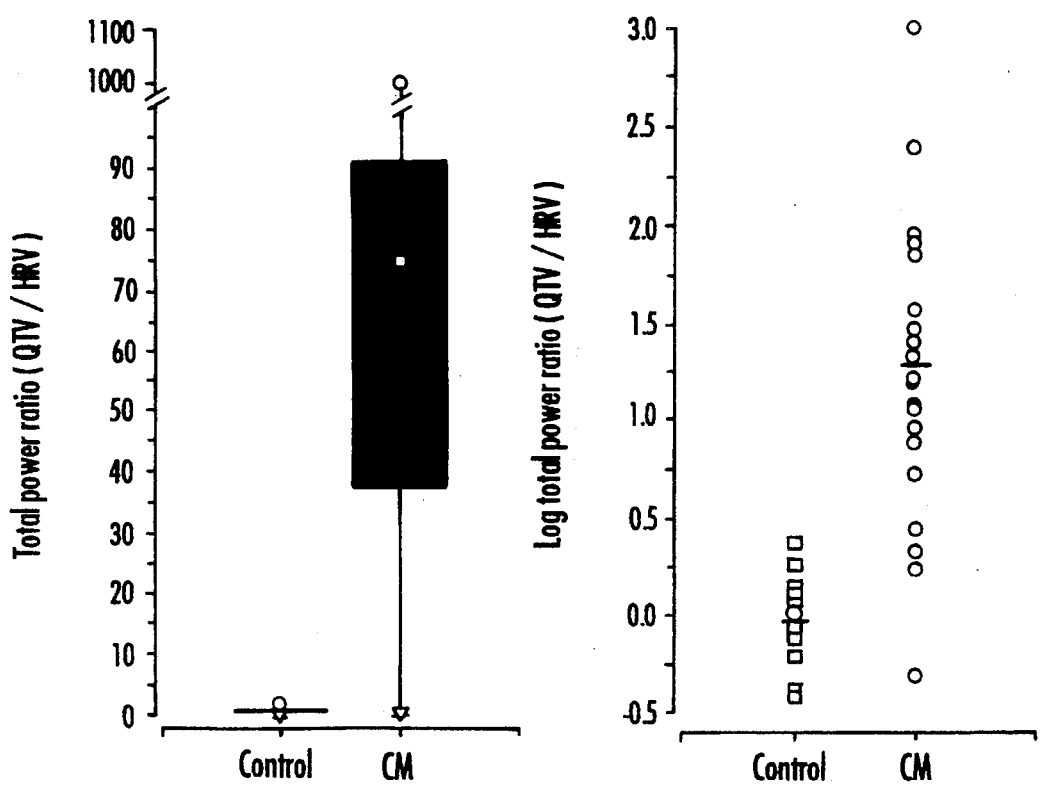
FIG. 7 shows a variance in the quotient over several orders of magnitude and a normal distribution of the logarithm of this quotient for each of the group with substantially little overlap between them.

In accordance with the method for measuring QT intervals in accordance with the present invention, an index of normalized QT variability was developed, based on the quotient between QTV and HRV power. The box plot in the left panel of FIG. 7 shows that among patients with DCM, the quotient itself varies over several orders of magnitude with a very skewed distribution, as indicated by the break in the vertical axis. The right panel of FIG. 7 shows that the QTVI, the logarithm of this quotient (see equation 4), is essentially normally distributed for each of the two groups with little overlap between them. The difference in the QTVI between the two groups is significant at the p<0.001 level. The degree of cardiac electrical instability and risk of arrhythmia is quantified the QTVI. The QTVI, however, can be modified to be insensitive to changes in mean HR and mean QT by normalizing QT variability power and HR variablity power by their respective means.

Example 4

Figure 8:
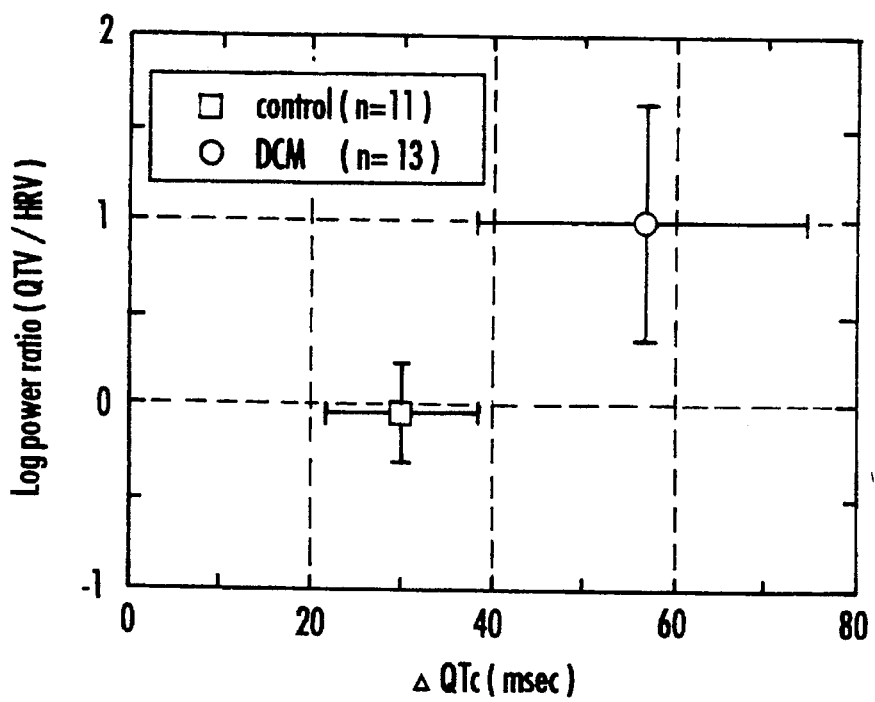
FIG. 8 show QT dispersions and QTVI in DCM patients compared with controls from tests conducted to determine if QT dispersion with DCM is associated with elevated QTVI.

Spatial QT dispersion has been shown to be increased in patients with heart failure and predictive of SCD in this group. In a pilot study in a small group of DCM patients and controls, the association of increased QT dispersion coupled with DCM and elevated QTVI were tested. QT dispersion was measured manually as the difference between maximum and minimum corrected QT interval among the 12 standard surface EGG leads. These results are shown in FIG. 8, and demonstrate concomitant increases in QT dispersion and QTVI in DCM patients compared with controls, and are believed to indicate that increased spatial and temporal dispersion of refractoriness go hand-in-hand in the setting of diseased myocardium. Although not wishing to be bound by any particular theory, their coexistence may serve to further promote arrhythmogenesis.

Having thereby described the subject matter of the present invention, it should be apparent that many substitutions, modifications and variations of the invention are possible in light of the above teachings. It is, therefore to be understood that the invention is taught and described here and is only to be limited to the extent of breadth and scope of amended claims.

What is claimed is:

1. A method for analyzing electrocardiograph signals to determine beat-to-beat QT interval variability, said method comprising:
    a) sensing fluctuations in voltage resulting from electrical activity of a heart over a predetermined time period as signals having an analog value;
    b) converting said signals having an analog value to digital values defined as x(n), where n is a sample number by sampling said analog signal with a fixed digitization interval $\Delta t$;
    c) analyzing said digital values, said analyzing comprising:
        i) identifying a time of each R wave of a heartbeat using a peak detection algorithm, wherein $T_i$ is defined as a time location for beat i;
        ii) defining a template QT interval, $\phi(n)$ for a heartbeat defined as beat number k, by selecting a beginning of a QRS complex, $n_0$, and an end point of a T wave, $n_1$, for said heartbeat wherein: $\phi(n)=x(n)$ from $n=n_0$ to $n=n_1$;
        iii) determining a QT interval for all other heartbeats by finding an optimally time-altered version of a T wave of each beat i that substantially matches a template T wave of beat wherein a QT interval determined for beat i is defined as $QT_i$.

2. The method of claim 1, wherein said fluctuations in voltage are sensed by leads.

3. The method of claim 2, wherein said leads comprise leads selected from the group consisting of surface leads and sub-surface leads.

4. The method of claim 3, wherein said leads comprise a ventricular leads selected from the group consisting of unipolar ventricular leads and bipolar ventricular leads endocardial ventricular leads, and epicardial ventricular leads.

5. The method of claim 4, wherein said ventricular lead is operably connected to an implanted apparatus.

6. The method of claim 5, wherein said implanted apparatus is selected from the group consisting of a pacemaker, and a defibrillator.

7. The method of claim 3, wherein said leads are surface leads selected from the group consisting of surface no. 1 leads and surface no. 2 leads, said leads being operably connected to an electrocardiograph, and said method comprising obtaining an electrocardiogram showing said fluctuation in voltage.

8. The method of claim 1, where $QT_i$ is taken as $\hat{\alpha}_i \cdot (n_1 - n_0) \cdot \Delta t$, where $\hat{\alpha}_i$ is the value of time-alteration factor $\alpha$ that minimizes an error functions $\epsilon_i(\alpha)$ for beat i.

9. The method of claim 8, wherein the error function $\epsilon_i(\alpha)$ is defined as:

$$\epsilon_i(\alpha) = \sum_{j=n_\nabla}^{n_1 - T_k} [\Phi(T_k + j) - \chi(T_i + \alpha j)]^2$$

where $n_\nabla$ represents a blanking period, set for a time to avoid inclusion of the QRS complex in the error function calculation, and $T_k$ is a time location of an R wave for a template beat k.

10. The method of claim 8, wherein the error function $\epsilon_i(\alpha)$ is minimized by searching over a domain of values for $\alpha$ as follows:

a) $\alpha$ is initially set to 1.0, and a search step size $\Delta\alpha$ is initially set to 0.02;

b) $\epsilon$ is computed for three values as follows:

$\epsilon_a = \epsilon_i(\alpha - \Delta\alpha)$ $\epsilon_b = \epsilon_i(\alpha)$ $\epsilon_c = \epsilon_i(\alpha + \Delta\alpha)$ c) based on a value of $\epsilon_a$, $\epsilon_b$, and $\epsilon_c$ which is the lowest, conducting a search as follows:
   i) $\alpha$ is reset to $\alpha - \Delta\alpha$ when $\epsilon_a$ is the lowest,
   ii) $\Delta\alpha$ is reset to $\Delta\alpha/2$ when $\epsilon_b$ is the lowest, and
   iii) $\alpha$ is reset to $\alpha + \Delta\alpha$ when $\epsilon_c$ is the lowest; and d) if ending the search with $\hat{\alpha}_i$ taken as the final value of $\alpha$ that was used $\Delta\alpha < 0.0001$; and continuing the search if $\Delta\alpha > 0.0001$ by returning to step b.

11. The method of claim 2, wherein said leads are surface electrodes attached to body limbs or chest, and operably connected to an electrocardiograph.

12. The method of claim 2, further comprising determining a QT interval variability index (QTVI) based on the series of QT interval values derived from an electrocardiographic signal.

13. The method of claim 12, wherein the QTVI is defined as:

$$QTVI = \log_{10}(P_{QTV}/P_{HRV})$$

where $P_{QTV}$ and $P_{HRV}$ represent total QT and heart rate variability power, respectively.

14. The method of claim 11, wherein the QTVI is defined as:

$$QTVI = \log_{10}\left[\frac{P_{QTV}/<QT>^2}{P_{HRV}/<HR>^2}\right]$$

where $P_{QTV}$ and $P_{HRV}$ represent total QT and heart rate variability power, respectively, and $<QT>$ and $<HR>$ represent QT interval and heart rate, respectively.

15. The method of claim 1 further comprising determining risk of malignant arrhythmias.

16. A method for analyzing electrocardiograph signals, said method comprising:

a) sensing fluctuations in voltage resulting from electrical activity of a heart over a time period of about 256 seconds as signals having an analog value;

b) converting said signals having an analog value to digital values corresponding substantially to said analog value of said signals;

c) recording said digital values in a record;

d) analyzing said digital values of said record, said analyzing comprising:
   i) identifying a time of each R wave of a heartbeat;
   ii) defining a template QT interval for a heartbeat by selecting a beginning of a QRS complex and an end of a T wave for said heartbeat;
   iii) determining an alteration value selected from the group consisting of an elongation of a heartbeat in time and a compression of a heartbeat in time as an error function for said heartbeat;
   iv) performing a search to determine a minimal value for said error function;
   v) assessing changes in QT interval for each heartbeat using said entire T wave; and utilizing a region of said QT template from $n=T_k+n_\nabla$ to $n=n_1$, where $n_\nabla$ comprises a preset delay, to match all heartbeats to said QT template wherein: i) comprises identifying a time for each R wave using a peak detection algorithm wherein $T_i$ are time locations; and ii) comprises selecting a beginning of a QT interval and an end of a QT interval for said heartbeat, wherein k is said heartbeat, so a QT template is $\phi(n)$, where n is a sample number such that:

$$\phi(n) = x(n) \text{ from } n=n_0 \text{ to } n=n_1$$

where x(n) is one of said signals, and $n_0$ and $n_1$ are said beginning of said QT interval and end of said QT interval, respectively; said QT template comprises $N = n_1 - n_0$ points and said template QT interval duration comprises $N \Delta t$ where $\Delta t$ is a digitization interval; and said digitization interval comprises about 1 msec.

* * * * *